(12) United States Patent
Tokuyasu et al.

(10) Patent No.: US 7,842,843 B2
(45) Date of Patent: Nov. 30, 2010

(54) MIXTURE CONTAINING 1,3-BUTADIENE AND PROCESS FOR PRODUCING THE SAME

(75) Inventors: Jin Tokuyasu, Kurashiki (JP); Hideharu Iwasaki, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 140 days.

(21) Appl. No.: 11/564,583

(22) Filed: Nov. 29, 2006

(65) Prior Publication Data

US 2007/0123738 A1    May 31, 2007

(30) Foreign Application Priority Data

Nov. 30, 2005    (JP) .............................. 2005-346573

(51) Int. Cl.
*C07C 41/06* (2006.01)
(52) U.S. Cl. ...................... 568/657; 568/688; 568/690
(58) Field of Classification Search ...................... None
See application file for complete search history.

(56) References Cited

U.S. PATENT DOCUMENTS

| | | | |
|---|---|---|---|
| 3,076,858 A * | 2/1963 | Frevel et al. ................. | 585/262 |
| 3,200,167 A * | 8/1965 | Manfred ....................... | 585/262 |
| 3,328,477 A * | 6/1967 | Taylor et al. ................. | 585/260 |
| 3,505,304 A * | 4/1970 | Davison et al. ............... | 526/77 |
| 4,818,431 A | 4/1989 | Eidenschink et al. | |
| 5,480,580 A | 1/1996 | Sakashita et al. | |
| 5,510,541 A * | 4/1996 | Patrini et al. ................. | 568/654 |
| 5,600,045 A * | 2/1997 | Van Der Aalst et al. ..... | 585/261 |
| 5,877,363 A | 3/1999 | Gildert et al. | |
| 6,225,515 B1 | 5/2001 | Cottrell | |
| 6,388,150 B1 | 5/2002 | Overbeeck et al. | |
| 6,417,419 B1 | 7/2002 | Abrevaya et al. | |
| 2003/0036669 A1 | 2/2003 | Ryu et al. | |
| 2005/0240039 A1 | 10/2005 | Rottger et al. | |

FOREIGN PATENT DOCUMENTS

| | | |
|---|---|---|
| EP | 0 409 066 A2 | 1/1991 |
| EP | 0 641 850 A1 | 3/1995 |
| EP | 0 967 261 A1 | 12/1999 |
| EP | 1 591 162 A1 | 11/2005 |
| EP | 1 760 061 A1 | 3/2007 |
| JP | 59-164788 | 9/1984 |
| JP | 3-128371 | 5/1991 |
| JP | 4-211678 | 8/1992 |
| JP | 4-364176 | 12/1992 |
| JP | 7-72442 | 3/1995 |
| JP | 29-748052 | 11/1999 |
| JP | 29-748242 | 11/1999 |
| JP | 2000-8040 | 1/2000 |
| JP | 2001-500522 | 1/2001 |
| JP | 2004-292774 | 10/2004 |
| JP | 2005095850 * | 4/2005 |
| JP | 2006001867 A * | 1/2006 |
| WO | WO 94/26720 | 11/1994 |
| WO | WO 98/12160 | 3/1998 |
| WO | WO 00/43337 | 7/2000 |
| WO | WO 2004/065006 A1 * | 5/2004 |

OTHER PUBLICATIONS

Hori et al., computer generated English translation and English abstract of JP 2006-1867 A, published Jan. 2006.*
Patent abstract of JP 2005-095850, published Apr. 2005.*
Lectures on Catalyst Chemistry "Engineering Series 1" Catalyst Design, vol. 5, 1985 (with partial English Translation).
Arno Behr, et al., "Palladium-Catalyzed Telomerization of Butadiene with Ethylene Glycol in Liquid Single Phase and Biphasic Systems: Control of Selectivity and Catalyst Recycling", Journal of Molecular Catalysis A: Chemical, vol. 197, XP002317198, Apr. 18, 2003, pp. 101-113.

* cited by examiner

*Primary Examiner*—Rosalynd Keys
(74) *Attorney, Agent, or Firm*—Oblon, Spivak, McClelland, Maier & Neustadt, L.L.P.

(57) ABSTRACT

To provide a C4 fraction that contains significantly reduced amounts of butynes and methylallene and to provide a process for low-cost and effective production of ethers in which the C4 fraction is used as the starting material for a telomerization process.

A mixture containing 25 to 80 mass % 1,3-butadiene, 13 to 68 mass % butenes and 2 to 15 mass % butanes with butynes and methylallene being contained in amounts of 50 ppm or less and 5 to 800 ppm, respectively.

1 Claim, 3 Drawing Sheets

MIXTURE CONTAINING 1,3-BUTADIENE AND PROCESS FOR PRODUCING THE SAME

TECHNICAL FIELD

The present invention relates to which is consisted of a new mixture that contains 1,3-butadiane. The invention also relates to a process for producing such a mixture.

TECHNICAL BACKGROUND

Naphtha cracking has allowed large-scale production of the distilled fraction composed primarily of C4 compounds (the distilled fraction will be referred to as "C4 fraction", hereinafter.): The C4 fraction has become readily available on industrial scale. Although the C4 fraction contains butenes and 1,3-butadiene which are useful to industrial raw materials, it also contains butynes, the compounds that, when subjected to later telomerization and other chemical processes, will not only form explosive materials, but also cause to decrease the activity of catalysts used for these reactions.

Thus, several approaches have been proposed to remove butynes from the C4 fraction. These techniques involve selectively hydrogenating butynes to convert them into olefins, which are then separated by fractional distillation and purified (See, for example, Patent Documents 1 and 2).

[Patent Document 1] U.S. Pat. No. 6,225,515

[Patent Document 2] Japanese Translation of PCT International Application No. 2001-500522

DISCLOSURE OF THE INVENTION

Problems Addressed by the Invention

However, the hydrogenation catalyst described in Patent Document 1 can only selectively hydrogenate butynes, but not methylallene. Studies conducted by the present inventors have revealed that methylallene, unless contained in a specific range of amounts, likewise leads to decrease the activity of the catalysts used in the later telomerization process. Removal of methylallene by fractional distillation requires a separate distillation tower with a large number of distillation trays, leading to an increase in the production cost.

On the other hand, the hydrogenation catalyst described in Patent Document 2 can hydrogenate both butynes and methylallene. Nonetheless, methylallene still remains in the mixture after processing with the catalyst at a concentration of 1000 ppm to 3000 ppm. When this mixture is subjected to the telomerization process, the activity of the catalyst is again decreased and undesired side-reactions will take place. This is believed to be because residual methylallene easily forms complexes with noble metals such as palladium. The problem of decreased catalyst activity and side-reactions are particularly serious when the telomerization process is carried out at low catalyst concentrations to minimize production cost.

Thus, there is a significant industrial need for a mixture that is prepared from the C4 fraction and yet contains butynes and methylallene in amounts small enough not to affect the activity of the telomerization catalyst. A process for producing such a mixture is also needed. On the other hand, it is known that highly pure 1,3-butadiene (with almost 99% or higher purity and containing approximately 20 ppm butynes) is industrially available and can be used in the telomerization process after removal of butynes. The highly pure 1,3-butadiene is too costly, however: It is three to four times as expensive as the C4 fraction. Therefore, it is desirable to develop simple techniques to remove butynes and methylallene from the inexpensive C4 fraction. Such techniques will be highly useful in industrial applications.

Accordingly, it is an object of the present invention to provide a mixture that is obtained by removing butynes from the C4 fraction and has the amount of methylallene reduced to a degree that has never been achieved before (The mixture may be referred to as "the mixture of the present invention," hereinafter).

Means to Solve the Problems

The foregoing object is achieved by the provision of the following:

[1] A mixture comprising 25 to 80 mass % 1,3-butadiene, 13 to 68 mass % butenes, 2 to 15 mass % butanes, 50 ppm or less butynes and 5 to 800 ppm methylallene.

[2] The mixture according to claim 1, obtained by a process comprising:
providing through naphtha cracking a distilled fraction of naphtha composed mainly of C4 compounds; and
selectively hydrogenating butynes and methylallene contained in the fraction with a copper catalyst containing an alkaline earth metal.

[3] A process for producing a mixture comprising 25 to 80 mass % 1,3-butadiene, 13 to 68 mass % butenes, 2 to 15 mass % butanes, 50 ppm or less butynes and 5 to 800 ppm methylallene, the process comprising:
providing through naphtha cracking a distilled fraction of naphtha composed mainly of C4 compounds; and
selectively hydrogenating butynes and methylallene contained in the fraction with a copper catalyst containing an alkaline earth metal.

[4] A process for producing a mixture comprising 25 to 80 mass % 1,3-butadiene, 13 to 68 mass % butenes, 2 to 15 mass % butanes, 50 ppm or less butynes and 5 to 800 ppm methylallene, the process comprising:
providing through naphtha cracking a distilled fraction of naphtha composed mainly of C4 compounds;
removing butynes from the fraction to obtain a mixture; and
selectively hydrogenating methylallene contained in the mixture with a copper catalyst containing an alkaline earth metal.

[5] A process for producing a mixture comprising 25 to 80 mass % 1,3-butadiene, 13 to 68 mass % butenes, 2 to 15 mass % butanes, 50 ppm or less butynes and 5 to 800 ppm methylallene, the process comprising:
providing through naphtha cracking a distilled fraction of naphtha composed mainly of C4 compounds;
selectively hydrogenating butynes contained in the fraction with an alkaline earth metal-free copper catalyst to obtain a mixture; and
selectively hydrogenating residual butynes and methylallene in the mixture with copper catalyst containing an alkaline earth metal.

[6] A process for producing a mixture comprising 25 to 80 mass % 1,3-butadiene, 13 to 68 mass % butenes, 2 to 15 mass % butanes, 50 ppm or less butynes and 5 to 800 ppm methylallene, the process comprising:
providing through naphtha cracking a distilled fraction of naphtha composed mainly of C4 compounds;

selectively hydrogenating butynes contained in the fraction with an alkaline earth metal-free copper catalyst to reduce butynes to 50 ppm or less; and selectively hydrogenating the fraction with copper catalyst containing an alkaline earth metal.

According to the present invention, an ether can be produced that is represented by the following general formula (II) (referred to as "ether (II)", hereinafter):

(II)

wherein $R^a$ is a substituted or unsubstituted alkyl group or a substituted or unsubstituted aryl group, by a process comprising:

providing a mixture comprising 25 to 80 mass % 1,3-butadiene, 13 to 68 mass % butenes, 2 to 15 mass % butanes, 50 ppm or less butynes and 5 to 800 ppm methylallene; and performing a telomerization process in the presence of a palladium catalyst using the mixture and a hydroxyl compound represented by the following general formula (I) (referred to as "hydroxyl compound (I)", hereinafter):

$$R^aOH, \quad (I)$$

wherein $R^a$ is a substituted or unsubstituted alkyl group or a substituted or unsubstituted aryl group.

ADVANTAGES OF THE INVENTION

The present invention enables cost-effective, simple and easy industrial production of a mixture that is obtained by removing butynes from inexpensive C4 fraction and reducing methylallene to a predetermined range of amounts from the C4 fraction removed butynes.

Unlike the conventional C4 fraction, the mixture of the present invention does not cause a decrease in the activity of the telomerization catalyst. As a result, the telomerization process can proceed effectively at low concentrations of the catalyst.

BEST MODE FOR CARRYING OUT THE INVENTION

C4 Fraction Used as the Starting Material

As described above, the mixture of the present invention is prepared from the distilled fraction (C4 fraction) obtained by cracking of naphtha. The C4 fraction is composed primarily of C4 compounds.

The C4 fraction generally comprises 1,3-butadiene; 1-butene, 2-butene and isobutylene (collectively referred to as "butenes"); butane and isobutane (collectively referred to as "butanes"); 1-butyn-3-ene, 1-butyne and 2-butyne (collectively referred to as "butynes"); and methylallene. It also contains methylacetylene, methylcyclopropane, 2,2-dimethylcyclopropane, isopentane and so on. The components of the C4 fraction for use in the present invention may be contained in any proportions as long as 50 mass % or more of the fraction is composed of compounds with four carbon atoms. The C4 fraction may be a commercially available (distributed) product: For example, such products as B-B fraction (marketed under trade name of Crude C4; produced by SHOWA DENKO), BB fraction (product name, produced by MITSUI CHEMICALS) and BB fraction (product name, produced by TOSOH) are commercially available. One example of commercially available (distributed) C4 fraction is composed of 47 mass % 1,3-butadiene, 50 mass % butenes, 2 mass % butanes, 300 ppm butynes, and 2500 ppm methylallene. Another example is composed of 42 mass % 1,3-butadiene, 35 mass % butenes, 22 mass % butanes, 200 ppm butynes, and 1200 ppm methylallene.

Composition of C4 fraction can readily be analyzed by gas chromatography.

A typical analysis can be performed using the following procedure:

Instrument: GC-14B (manufactured by SHIMADZU);

Column: DB-WAX (length=10 m, inner diameter=0.25 mm, film thickness=0.25 μm) (manufactured by AGILENT TECHNOLOGIES);

Conditions for analysis: injection temp.=220° C.; detection temp.=250° C.; temperature condition: maintained at 40° C. for 8 min→temperature raised at a rate of 15° C./min→maintained at 240° C. for 30 min.

[Process for Producing the Mixture of the Invention]

The mixture of the present invention is obtained by selectively hydrogenating butynes and methylallene in the C4 fraction with a copper catalyst containing an alkaline earth metal. The C4 fraction may have the butynes decreased or eliminated prior to its use as the starting material.

The following techniques are used to selectively remove butynes from the C4 fraction:

[i] Selective hydrogenation of butynes using a copper catalyst containing zinc, silver, platinum, iron, manganese, cobalt, nickel, palladium, chromium, molybdenum and so on (However, the catalyst does not have an alkaline earth metal. And the catalyst may be carried by a suitable carrier, including, but not limited to, alumina, silica, silica-alumina, titania, zirconia, active carbon and so on.). Specifically, the reaction is carried out in the presence of a catalyst such as KLP-60™ catalyst (produced by UOP) at a temperature of 10 to 60° C. and under a pressure of 0.005 to 10 MPa (partial pressure of hydrogen=0.002 to 6 MPa). This technique causes little loss of 1,3-butadiene (See, for example, Patent Document 1).

[ii] Distillation using a distillation tower with at least 20 trays.

[iii] Other known techniques.

Examples of the alkaline earth metal in the above-described alkaline earth metal-containing copper catalyst include beryllium, magnesium, calcium, strontium, and barium. These alkaline earth metals may be contained in the catalyst either individually or in combination of two or more. And the alkaline earth metal(s) may be present in any form, for example, the form of salts formed with the carriers (e.g., silicates and aluminates), oxides, hydroxides, and carbonates and so on.

While the alkaline earth metal may be contained in the copper catalyst in any amount, it is typically contained in an amount in the range of 0.1 mass % to 30 mass %, and preferably in the range of 0.3 mass % to 20 mass % with respect to the total mass of the alkaline earth metal-containing copper catalyst. When the amount of the alkaline earth metal falls within this range, the catalyst remains stable on the carrier and is less susceptible to changes caused by falling off or dissolving of the alkaline earth metal.

The alkaline earth metal-containing copper catalyst is typically carried by a carrier. Examples of the carrier include, but are not limited to, alumina, silica, silica-alumina, titania, zirconia, and active carbon. Of these, alumina, silica and silica-alumina are preferred to ensure suppression of hydrogenation and polymerization of 1,3-butadiene and to ensure mechanical strength, heat-resistance and chemical stability.

While the carrier may be provided in any form, it has a surface area typically in the range of 3 $m^2/g$ to 1000 $m^2/g$, and preferably in the range of 20 $m^2/g$ to 500 $m^2/g$. When the surface area of the carrier falls within this range, copper and alkaline earth metal remain stable on the carrier.

The amount of copper carried by the carrier is typically in the range of 0.1 mass % to 85 mass % with respect to the total mass of the alkaline earth metal-containing copper catalyst. In view of the reactivity and the mechanical strength, the amount is preferably in the range of 1 mass % to 80 mass %, and more preferably in the range of 5 mass % to 70 mass % with respect to the total mass of the alkaline earth metal-containing copper catalyst.

Copper is typically contained in the copper catalyst in the form of a simple substance of copper, copper oxide, or copper hydroxide.

Copper may be contained in the copper catalyst in any form: It may be carried by the carrier as particles. In such a case, the copper particles have an average particle size typically in the range of 10 nm to 1000 nm, and preferably in the range of 30 nm to 800 nm.

In one exemplary process, the alkaline earth metal-containing copper catalyst is produced as follows. First, copper and a salt of an alkaline earth metal are dissolved in water. To this solution, a silica or alumina sol is added and the mixture is warmed to 50° C. or above to thoroughly disperse the sol. A base such as sodium hydroxide or ammonia is then added to obtain a black solid. The solid product is filtered, washed, and dried while being kneaded in a kneader. This gives the catalyst (See, for example, Shokubai kagaku kouza, Shokubai sekkei (Lectures on catalyst, Catalyst design) Vol. 5 (1985): pp 42-43 and pp 58-59).

Examples of commercially available products of alkaline earth metal-containing copper catalyst for use in the present invention are F40-5, F40A-8, and F40A-9 marketed from NIKKI CHEMICAL (Each a catalyst number).

Preferably, the alkaline earth metal-containing copper catalyst is activated prior to use in the hydrogenation process. For example, the catalyst can be activated by treating it at 60° C. to 200° C., optionally in the presence of liquid paraffin, polyethylene glycol, or polypropylene glycol, under a hydrogen atmosphere, typically from 30 minutes to 8 hours. When used, liquid paraffin, polyethylene glycol or polypropylene glycol is preferably used in an amount in the range of 1 part by mass to 20 parts by mass with respect to 1 part by mass of the copper catalyst.

We will now describe conditions for selective hydrogenation of butynes and methylallene in the C4 fraction using the alkaline earth metal-containing copper catalyst (The process is referred to as "Process A", hereinafter).

The reaction pressure in the process A is typically in the range of 0.05 MPa to 20 MPa and preferably in the range of 0.1 MPa to 10 MPa. The partial pressure of hydrogen is typically in the range of 0.01 MPa to 8 MPa and preferably in the range of 0.1 MPa to 6 MPa.

The reaction temperature is preferably in the range of 10° C. to 80° C. and preferably in the range of 20° C. to 70° C. The reaction proceeds smoothly at temperatures equal to or above the lower limit of the specified range, so it is favorable economically. 1,3-Butadiene is less susceptible to hydrogenation at temperatures equal to or below the upper limit of the specified range, resulting in little loss of 1,3-butadiene from the starting material.

While the process A is preferably carried out in a hydrogen atmosphere, nitrogen, argon and other inert gases may also be present.

The amount of the alkaline earth metal-containing copper catalyst is preferably in the range of 0.001 parts by mass to 100 parts by mass, and more preferably in the range of 0.002 parts by mass to 50 parts by mass, with respect to 1 part by mass of methylallene contained in the starting material.

The process may be carried out in any manner, for example, a batch process or a continuous process. For example, a typical batch process is carried out as follows. A predetermined amount of the alkaline earth metal-containing copper catalyst is placed in a pressure-resistant reactor (pressure rating=30 MPa) equipped with a stirrer. When necessary, a predetermined amount of liquid paraffin, polyethylene glycol, or polypropylene glycol is added to make a dispersion. With the atmosphere in the reactor replaced with an inert gas such as nitrogen and argon, the reactor is heated to a predetermined temperature and hydrogen is passed through the dispersion at a liquid hourly space velocity (LHSV) of 0.1 $h^{-1}$ over a predetermined time period. This activates the catalyst. After the catalyst has been activated, the temperature of the dispersion is decreased to a predetermined reaction temperature and the C4 fraction is then added for hydrogenation. The reaction is allowed to proceed under a predetermined partial pressure of hydrogen and a predetermined reaction pressure. When necessary, an inert gas such as nitrogen and argon is introduced to establish the required pressure.

A typical continuous process is carried out as follows. The alkaline earth metal-containing copper catalyst is placed in a flow-type pressure-resistant reactor (pressure rating=30 MPa). The atmosphere in the reactor is replaced with an inert gas such as nitrogen and argon, and the reactor is heated to a predetermined temperature while hydrogen and the above-stated inert gas are flowed through the reactor at LHSV=0.1 $h^{-1}$ under a predetermined reaction pressure and a predetermined hydrogen partial pressure. The amount of the introduction of the above-stated inert gas is gradually decreased until the atmosphere in the reaction vessel is completely replaced with hydrogen. The catalyst is activated after a predetermined period of time. After the catalyst has been activated, the temperature of the reactor is decreased to a predetermined temperature. Hydrogenation is then carried out by introducing the C4 fraction and hydrogen from the bottom of the reactor to maintain a predetermined reaction pressure and a predetermined hydrogen partial pressure.

The mixture of the present invention obtained from the C4 fraction in the above-described manner is a novel mixture that contains 25 to 80 mass % 1,3-butadiene, 13 to 68 mass % butenes and 2 to 15 mass % butanes with butynes and methylallene being contained in amounts of 50 ppm or less and 5 to 800 ppm, respectively. This mixture is suitable for use as the starting material for the telomerization process since the decrease in the activity of the telomerization catalyst can be significantly reduced by the use of the mixture. A more preferred composition of the mixture of the present invention for use in the telomerization process comprises 25 to 80 mass %

1,3-butadiene, 13 to 68 mass % butanes, and 2 to 15 mass % butanes with 30 ppm or less butynes and 5 to 500 ppm methylallene. A still more preferred composition of the mixture comprises 25 to 80 mass % 1,3-butadiene, 13 to 68 mass % butenes and 2 to 15 mass % butanes with 20 ppm or less butynes and 5 to 200 ppm methylallene. A particularly preferred composition of the mixture comprises 25 to 80 mass % 1,3-butadiene, 13 to 68 mass % butenes and 2 to 15 mass % butanes with 10 ppm or less butynes and 5 to 100 ppm methylallene.

[Telomerization Process]

The term "telomerization process" as used herein refers to a chemical process in which a conjugated diene compound (i.e., 1,3-butadiene contained in the mixture of the present invention) incorporates a nucleophilic agent and oligomerizes.

As described above, the mixture of the present invention is suitable for use in the telomerization process. Specifically, the mixture of the present invention is telomerized with a hydroxyl compound (I) in the presence of a palladium catalyst and an optional ligand, an optional basic compound and an optional solvent. In this manner, an ether (II) is produced efficiently (The telomerization process is referred to as "telomerization process B", hereinafter). We will now describe the telomerization process B.

The alkyl group represented by $R^a$ is preferably an alkyl group having 1 to 8 carbon atoms. Examples include methyl group, ethyl group, n-propyl group, isopropyl group, n-butyl group, isobutyl group, s-butyl group, t-butyl group, n-pentyl group, n-hexyl group, n-heptyl group, n-octyl group, cyclopentyl group, cyclohexyl group, cycloheptyl group, and cyclooctyl group. These alkyl groups may be substituted. Examples of the substituent include halogen atom, such as fluorine atom, chlorine atom, bromine atom and iodine atom; aryl group, such as phenyl group, tolyl group and xylyl group; alkoxyl group, such as methoxy group, ethoxy group, propoxy group and isopropoxy group; 2-methoxyethyloxy group, 2-ethoxyethyloxy group; and hydroxyl group.

The aryl group represented by $R^a$ is preferably an aryl group having 6 to 14 carbon atoms. Examples include phenyl group, naphthyl group, phenanthryl group, and anthracenyl group. These aryl groups may be substituted. Examples of the substituent include halogen atom, such as fluorine atom, chlorine atom, bromine atom and iodine atom; alkyl group, such as methyl group, ethyl group, propyl group, isopropyl group, butyl group, isobutyl group, s-butyl group, t-butyl group, pentyl group, hexyl group, heptyl group and octyl group; alkoxyl group, such as methoxy group, ethoxy group, propoxy group and isopropoxy group; and hydroxyl group.

Specific examples of the hydroxyl compound (I) include methanol, ethanol, 1-propanol, 2-propanol, 2-methyl-1-propanol, 1-butanol, 2-butanol, pentanol, isopentyl alcohol, cyclopentanol, hexanol, 2-hexanol, cyclohexanol, 1-heptanol, 1-octanol, 2-octanol, 3-octanol, benzyl alcohol, phenethyl alcohol, phenol, ethylene glycol, diethylene glycol, propylene glycol, ethylene glycol monomethyl ether, ethylene glycol monoethyl ether, diethylene glycol monomethyl ether, diethylene glycol monoethyl ether, propylene glycol monomethyl ether, and propylene glycol monoethyl ether.

The amount of the hydroxyl compound (I) used in the telomerization process B is preferably in the range of 0.1 mol to 10 mol, and more preferably in the range of 0.5 mol to 5 mol, with respect to 1 mol of 1,3-butadiene contained in the mixture of the present invention.

Examples of the palladium catalyst used in the telomerization process B include palladium formate, palladium acetate, palladium chloride, palladium bromide, palladium carbonate, palladium sulfate, palladium nitrate, sodium chloropalladate, potassium chloropalladate, palladium acetylacetonate, bis(benzonitrile)palladium dichloride, bis(t-butylisocyanide)palladium dichloride, bis(dibenzilideneacetone)palladium, tris(dibenzilideneacetone)dipalladium, bis(1,5-cyclooctadiene)palladium, and tetrakis(triphenylphosphine)palladium. Of these catalysts, palladium acetate and palladium acetylacetonate are particularly preferred because of their availability and cost effectiveness.

The amount of the palladium catalyst as measured by palladium atoms is preferably in the range of 0.1 ppm to 100 ppm by mass and more preferably in the range of 10 ppm to 50 ppm by mass with respect to 1,3-butadiene contained in the mixture of the present invention.

In carrying out the telomerization process B, a ligand that forms coordinate bonds with the palladium atom in the palladium catalyst may be added to the reaction system. Examples of the ligand include phosphine compounds, phosphite compounds, and isocyanide compounds. Specific examples of the phosphine compounds include trimethylphosphine, triethylphosphine, tri-n-propylphosphine, tri-n-butylphosphine, triisobutylphosphine, tri-n-hexylphosphine, tri-n-octylphosphine, and tricyclohexylphosphine.

Specific examples of the phosphite compounds include trialkylphosphites, such as trimethylphosphite, triethylphosphite, tri-n-propylphosphite, triisopropylphosphite, tri-n-butylphosphite, tri-t-butylphosphite and tricyclohexylphosphite; and triarylphosphite, such as triphenylphosphite, tris(p-methoxyphenyl)phosphite, tris(o-methylphenyl)phosphite, tris(m-methylphenyl)phosphite, tris(p-methylphenyl)phosphite, tris(o-ethylphenyl)phosphite, tris(m-ethylphenyl)phosphite, tris(p-ethylphenyl)phosphite, tris(o-propylphenyl)phosphite, tris(m-propylphenyl)phosphite, tris(p-propylphenyl)phosphite, tris(o-isopropylphenyl)phosphite, tris(m-isopropylphenyl)phosphite, tris(p-isopropylphenyl)phosphite, tris(o-t-butylphenyl)phosphite, tris(p-t-butylphenyl)phosphite, tris(p-trifluoromethylphenyl)phosphite, tris(2,4-dimethylphenyl)phosphite, tris(2,4-di-t-butylphenyl)phosphate, and tris(2-t-butyl-4-methylphenyl)phosphite.

Specific examples of the isocyanide compounds include t-butylisocyanide, t-octylisocyanide, tritylisocyanide, 1-methylcyclohexylisocyanide, tris(methoxymethyl)methylisocyanide, tris(ethoxymethyl)methylisocyanide, tris(n-propoxymethyl)methylisocyanide, tris(isopropoxymethyl)methylisocyanide, tris(n-butoxymethyl)methylisocyanide, tris(s-butoxymethyl)methylisocyanide, and tris(t-butoxymethyl)methylisocyanide.

These ligands may be used either individually or in combination of two or more. When two or more ligands are used, they may be added to the reaction system either simultaneously or separately. When used, the ligand is used in an amount preferably in the range of 0.1 mol to 100 mol, and more preferably in the range of 1 mol to 20 mol, with respect to 1 mol of palladium atom contained in the palladium catalyst.

In the telomerization process B, a base may optionally be added to the reaction system.

Examples of such base include alkali metal hydroxides, such as lithium hydroxide, sodium hydroxide and potassium hydroxide; alkaline earth metal hydroxides, such as calcium hydroxide, magnesium hydroxide and barium hydroxide; alkali metal alkoxides, alkali metal phenoxides, alkali metal benzyloxides, alkaline earth metal alkoxides, alkaline earth metal phenoxides, and alkali earth metal benzyloxides such as lithium methoxide, sodium methoxide, sodium isopropoxide, sodium s-butoxide, sodium phenoxide, sodium benzyloxide, potassium methoxide, potassium ethoxide, potassium isopropoxide, potassium s-butoxide, potassium t-butoxide, potassium phenoxide, potassium benzyloxide, magnesium methoxide, magnesium ethoxide, magnesium isopropoxide, magnesium s-butoxide, magnesium t-butoxide, magnesium phenoxide, magnesium benzyloxide, calcium methoxide, calcium ethoxide, calcium isopropoxide, calcium s-butoxide, calcium t-butoxide, calcium phenoxide and calcium benzyloxide; ammonium compounds, such as tetramethylammonium hydroxide, tetraethylammonium hydroxide, tetra-n-propylammonium hydroxide, tetraisopropylammonium hydroxide, tetra-n-butylammonium hydroxide, benzyltrimethylammonium hydroxide, tetramethylammonium methoxide, tetramethylammonium ethoxide, tetramethylammonium n-propoxide, tetramethylammonium phenoxide, tetraethylammonium methoxide, tetraethylammonium ethoxide, tetraethylammonium n-propoxide, tetraethylammonium phenoxide, tetra-n-propylammonium methoxide, tetra-n-propylammonium ethoxide, tetra-n-butylammonium methoxide, tetra-n-butylammonium ethoxide, tetra-n-butylammonium phenoxide, benzyltrimethylammonium methoxide, benzyltrimethylammonium ethoxide and benzyltrimethylammonium phenoxide; phosphonium compounds, such as tetramethylphosphonium hydroxide, tetraethylphosphonium hydroxide, tetra-n-propylphosphonium hydroxide, tetraisopropylphosphonium hydroxide, tetra-n-butylphosphonium hydroxide, benzyltrimethylphosphonium hydroxide, tetraphenylphosphonium hydroxide, tetramethylphosphonium methoxide, tetraethylphosphonium methoxide, tetra-n-propylphosphonium methoxide, tetraisopropylphosphonium methoxide, tetra-n-butylphosphonium methoxide, tetra-n-butylphosphonium ethoxide, tetra-n-butylphosphonium phenoxide, benzyltrimethylphosphonium ethoxide, tetraphenylphosphonium methoxide, tetraphenylphosphonium ethoxide and tetraphenylphosphonium phenoxide; and nitrogen-containing heterocyclic aromatic compounds, such as pyridine, bipyridyl, pyrimidine, 2-(1-piperadinyl)pyrimidine and quinoline.

When used, the base is used in an amount preferably in the range of 0.1 mol to 10000 mol, and more preferably in the range of 1 mol to 1000 mol, with respect to 1 mol of palladium atom present in the palladium catalyst.

While the hydroxyl compound (I) may serve as a solvent in the telomerization process B, the process may be carried out in the presence of other solvent. Examples of the solvent that can be used in the telomerization process B include hydrocarbons, such as butane, isobutane, butene, isobutene, pentane, hexane, cyclohexane, benzene, toluene and xylene; halogenated hydrocarbons, such as dichloromethane, 1,2-dichloroethane and chloroform; ethers, such as tetrahydrofuran, dipentyl ether, dihexyl ether, diethylene glycol dimethyl ether, triethylene glycol dimethyl ether and tetraethylene glycol dimethyl ether; and amides, such as formamide, acetamide, N,N-dimethylformamide and 1-methyl-2-pyrrolidinone. These solvents may be used either individually or in combination of two or more solvents. While the solvents may be used in any amount, they are typically used in an amount in the range of 0.01 parts by mass to 10 parts by mass with respect to 1 part by mass of 1,3-butadiene contained in the mixture of the present invention.

The telomerization process B is carried out at a temperature preferably in the range of 0° C. to 150° C. and more preferably in the range of 20° C. to 110° C. The reaction time tends to become short at a temperature equal to or above the lower limit of the specified range. The generation of by-products tends to be suppressed at a temperature equal to or below the upper limit of the specified range.

The telomerization process B is typically carried out under a pressure in the range of 0.1 MPa to 3 MPa.

Preferably, the telomerization process B is carried out in an inert gas atmosphere, such as nitrogen and argon. The process may be carried out for any length of time.

The telomerization process B may be carried out in any manner, for example, a continuous process or a batch process. For example, a typical continuous process is carried out as follows. The above-described palladium catalyst, the hydroxyl compound (I) and if necessary, the ligand, the base and the solvent are mixed together. The mixture is continuously or intermittently added to a second mixture comprising the mixture of the present invention and the hydroxyl compound (I). The addition is done in a nitrogen atmosphere at a predetermined temperature under a predetermined pressure. Upon completion of the reaction, the reaction mixture is continuously or intermittently removed from the reaction system.

A typical batch process is carried out as follows: The above-described palladium catalyst, the hydroxyl compound (I) and if necessary, the ligand, the base and the solvent are mixed together. To the resulting mixture, the mixture of the present invention is added and the reaction is allowed to proceed at a predetermined temperature under a predetermined pressure.

The present inventors have discovered a way to effectively prevent the decrease in the activity of the telomerization catalyst when the telomerization process B uses an isocyanide compound as the ligand. Specifically, the hydroxyl compound (I), the palladium catalyst, the nitrogen-containing heterocyclic aromatic compound, the isocyanide compound, the base (other than the nitrogen-containing heterocyclic aromatic compounds) and if necessary, the solvent are mixed together to form a mixture. This mixture and the mixture of the present invention are fed to a reactor to carry out the telomerization reaction. In this manner, the decrease in the activity of the telomerization catalyst during the process is effectively prevented.

Upon completion of the reaction, the ether (II) is separated and purified from the reaction mixture. This is done by any suitable technique commonly used in the separation and purification of organic compounds. For example, the unreacted starting materials and the optionally used solvent are evaporated and the catalytic components (i.e., palladium catalyst and ligand) are separated from the resulting residue using thin-film evaporation, decantation, extraction, adsorption, or other proper techniques. The resulting residue is then purified by distillation, recrystallization, column chromatography or other techniques to give the desired ether (II) at high purity. The separated mixture containing the catalytic components can be recycled in the process of the present invention to produce ether.

EXAMPLES

The present invention will now be described in further detail with reference to examples, which are not intended to limit the scope of the invention in any way. Unless otherwise specified, the gas chromatography analysis performed in Reference Examples, Examples, and Comparative Examples follows the following procedure.

[Gas Chromatography Analysis]
Instrument: GC-14B (manufactured by SHIMADZU);
Column: DB-WAX (length=10 m, inner diameter=0.25 mm, film thickness=0.25 µm) (manufactured by AGILENT TECHNOLOGIES);
Conditions for analysis: injection temp.=220° C.; detection temp.=250° C.; temperature condition: maintained at 40°

C. for 8 min→temperature raised at a rate of 15° C./min→maintained at 240° C. for 30 min.

Material 1 and Material 2 used in Examples have respective compositions shown in Table 1 below.

TABLE 1

| | Content (by mass) | | | | |
|---|---|---|---|---|---|
| | 1,3-butadiene (mass %) | Butenes (mass %) | Butanes (mass %) | Butynes (ppm) | Methylallene (ppm) |
| Material 1 | 41.7 | 47.0 | 10.0 | 5363 | 1812 |
| Material 2 | 41.4 | 47.1 | 10.1 | 37 | 1861 |

*Commercial C4 fraction product (Trade Name: Crude C4, produced by SHOWA DENKO)

Reference Example 1

Preparation of Material 2 from Material 1

2.0 g of KLP-60™ catalyst (produced by UOP; the catalyst catalyzes selective hydrogenation of butynes) was placed in a 1000 ml autoclave. Subsequently, 10 ml liquid paraffin was added and the catalyst was activated at 100° C. for 1 hour in a hydrogen atmosphere. Once the catalyst had been activated, 500 ml (310 g) Material 1 was added and the reaction was allowed to proceed for 4 hours at 60° C. under a hydrogen pressure of 0.3 MPa, to make 308.7 g of a mixture (referred to as "Material 2", hereinafter). After completion of the reaction, a small portion of Material 2 was collected and was analyzed by gas chromatography. The results are shown in Table 1.

Example 1

2.0 g of a calcium-containing copper catalyst F40-5 (Catalyst number; calcium content=5 mass %; produced by NIKKI CHEMICAL) and 8.4 g (10 ml) of liquid paraffin were placed in a 1000 ml autoclave. The catalyst was activated in a hydrogen atmosphere at 100° C. for 1 hour. Once the catalyst had been activated, 500 ml (310 g) Material 1 was added and the reaction was allowed to proceed for 6 hours at 60° C. under a hydrogen pressure of 0.3 MPa. After completion of the reaction, a small portion of the resultant 307.6 g mixture was collected and was analyzed by gas chromatography. The results are shown in Table 2.

Example 2

The reaction was carried out in the same manner as in Example 1, except that Material 1 (500 ml; 310 g) was replaced with Material 2 (500 ml; 310 g). The resulting mixture was subjected to analysis. The results are shown in Table 2.

Example 3

The reaction was carried out in the same manner as in Example 2, except that the 2.0 g calcium-containing copper catalyst was replaced with 2.0 g of a magnesium-containing copper catalyst F20A-8 (Catalyst number; magnesium content=3 mass %; produced by NIKKI CHEMICAL). The resulting mixture was subjected to analysis. The results are shown in Table 2.

Example 4

The reaction was carried out in the same manner as in Example 2, except that the 2.0 g calcium-containing copper catalyst was replaced with 2.0 g of a barium-containing copper catalyst F40A-9 (Catalyst number; barium content=4 mass %; produced by NIKKI CHEMICAL). The resulting mixture was subjected to analysis. The results are shown in Table 2.

Comparative Example 1

The reaction was carried out in the same manner as in Example 2, except that the 2.0 g calcium-containing copper catalyst was replaced with 2.0 g of an unmodified copper catalyst E35S (Catalyst number; produced by NIKKI CHEMICAL). The resulting mixture was subjected to analysis. The results are shown in Table 2.

Comparative Example 2

The reaction was carried out in the same manner as in Example 2, except that the 2.0 g calcium-containing copper catalyst was replaced with 2.0 g of a zinc-containing copper catalyst N211 (Catalyst number; produced by NIKKI CHEMICAL). The resulting mixture was subjected to analysis. The results are shown in Table 2.

Comparative Example 3

The reaction was carried out in the same manner as in Example 2, except that the 2.0 g calcium-containing copper catalyst was replaced with 2.0 g of KLP-60™ (produced by UOP; the catalyst catalyzes selective hydrogenation of butynes). The resulting mixture was subjected to analysis. The results are shown in Table 2.

Comparative Example 4

The reaction was carried out in the same manner as in Example 2, except that the 2.0 g calcium-containing copper catalyst was replaced with 2.0 g of E144SDU (Catalyst number; produced by CALSICAT; a palladium-containing alumina catalyst that catalyzes selective hydrogenation of butynes (palladium content=0.5 mass %)). The resulting mixture was subjected to analysis. The results are shown in Table 2.

TABLE 2

| | | | Content (by mass) | | | | |
|---|---|---|---|---|---|---|---|
| | Material | Catalyst | 1,3-butadiene (mass %) | Butenes (mass %) | Butanes (mass %) | Butynes (ppm) | Methylallene (ppm) |
| Ref. Ex. 1 | Material 1 | KLP-60 ™ | 41.6 | 47.2 | 10.1 | 0 | 1806 |
| Ex. 1 | Material 1 | F40-5 | 41.1 | 47.7 | 10.2 | 7.3 | 84 |
| Ex. 2 | Material 2 | F40-5 | 40.6 | 47.2 | 11.7 | 0 | 20.1 |

TABLE 2-continued

| | | Content (by mass) | | | | |
|---|---|---|---|---|---|---|
| | Material | Catalyst | 1,3-butadiene (mass %) | Butenes (mass %) | Butanes (mass %) | Butynes (ppm) | Methylallene (ppm) |
| Ex. 3 | Material 2 | F40A-8 | 40.9 | 47.5 | 11.6 | 0 | 21.3 |
| Ex. 4 | Material 2 | F40A-9 | 40.7 | 47.7 | 11.9 | 0 | 20.6 |
| Comp. Ex. 1 | Material 2 | E35-S | 40.6 | 48.1 | 10.9 | 0 | 1851 |
| Comp. Ex. 2 | Material 2 | N211 | 40.2 | 48.3 | 10.2 | 0 | 1849 |
| Comp. Ex. 3 | Material 2 | KLP-60 ™ | 40.9 | 47.9 | 10.4 | 0 | 1852 |
| Comp. Ex. 4 | Material 2 | E144SDU | 39.9 | 48.6 | 10.6 | 0 | 1146 |

Example 5

Figure 1:
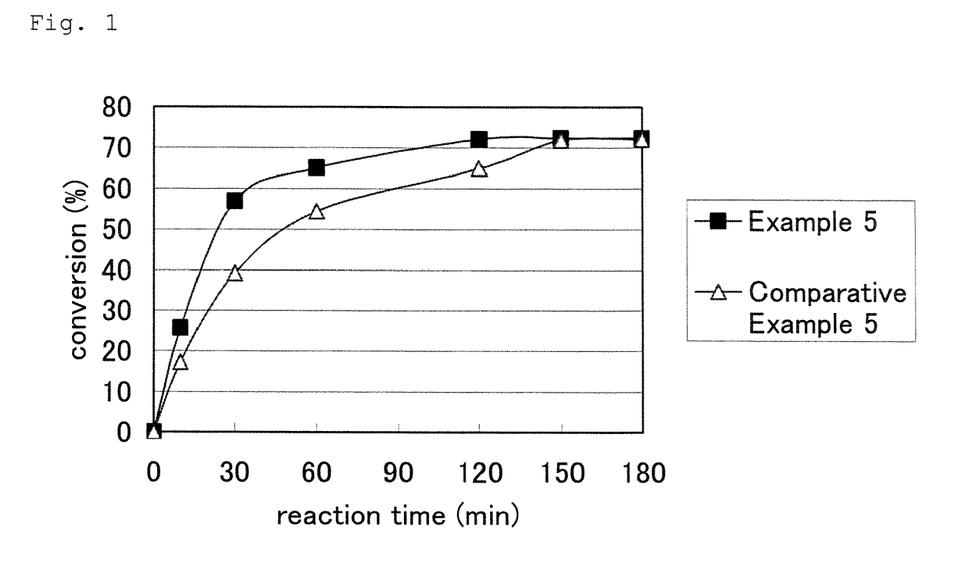
FIG. 1 shows results of Example 5 and Comparative Example 5.

The following ingredients were placed in a nitrogen-filled 5 L autoclave equipped with a magnetic stirrer to form a mixture: 60.6 mg (0.199 mmol) palladium acetylacetonate, 104 mg (0.398 mmol) triphenylphosphine, 3.84 g 28% methanol solution of sodium methoxide [equivalent to 1.07 g (19.9 mmol) sodium methoxide], 925 g (1.17 L, 28.9 mol) methanol, 1250 g (2.00 L) of the mixture of Example 2 [equivalent to 513 g (9.49 mol, 41 mass %) 1,3-butadiene] and 60 g tetraethylene glycol dimethyl ether as internal standard. The mixture was heated to 90° C. over a 50 minute period and the reaction was carried out for additional 3 hours. The heat generated during the reaction caused the internal temperature to rise to 112° C. The reaction mixture was analyzed by gas chromatography at intervals over the course of the reaction. The results are shown in FIG. 1.

After completion of the reaction, a portion of the reaction mixture was collected and was subjected to gas chromatography analysis, as described below. The analysis revealed that the following products were generated: 1-methoxy-2,7-octadiene (765 g, 5.46 mol, 79.4% select.), 3-methoxy-1,7-octadiene (60.6 g, 0.433 mol, 6.3% select.), 1,3,7-octatriene (103.8 g, 0.961 mol, 13.9% select.), and 4-vinylcyclohexene (1.48 g, 0.0137 mol, 0.2% select.).

[Gas Chromatography Analysis]

Instrument: GC-14B (manufactured by SHIMADZU);

Column: DB-WAX (length=30 m, inner diameter=0.25 mm, film thickness=0.25 μm) (manufactured by AGILENT TECHNOLOGIES);

Conditions for analysis: injection temp.=220° C.; detection temp.=250° C.; temperature initially maintained at 40° C. for 10 min→increased at a rate of 15° C./min→maintained at 250° C. for 40 min.

Comparative Example 5

The reaction and analysis were conducted in the same manner as in Example 5, except that the mixture obtained in Example 2 (500 ml; 310 g) was replaced with Material 2 (500 ml; 310 g). The results are shown in FIG. 1.

The results of Example 5 and Comparative Example 5 shown in FIG. 1 indicate that the activity of the catalyst remains higher when the mixture of the present invention is used (Example 5) than when Material 2 is directly used (Comparative Example 5). To be more specific, it takes approximately half time as long to reach the 65% conversion in Example 5 as it takes in Comparative Example 5.

Example 6

The reaction and analysis were conducted in the same manner as in Example 5, except that the 104 mg (0.398 mmol) triphenylphosphine was replaced with 33 mg (0.398 mmol) t-butylisocyanide. The results are shown in FIG. 2.

Comparative Example 6

The reaction and analysis were conducted in the same manner as in Example 6, except that the mixture obtained in Example 2 (500 ml; 310 g) was replaced with Material 2 (500 ml; 310 g). The results are shown in FIG. 2.

Figure 2:
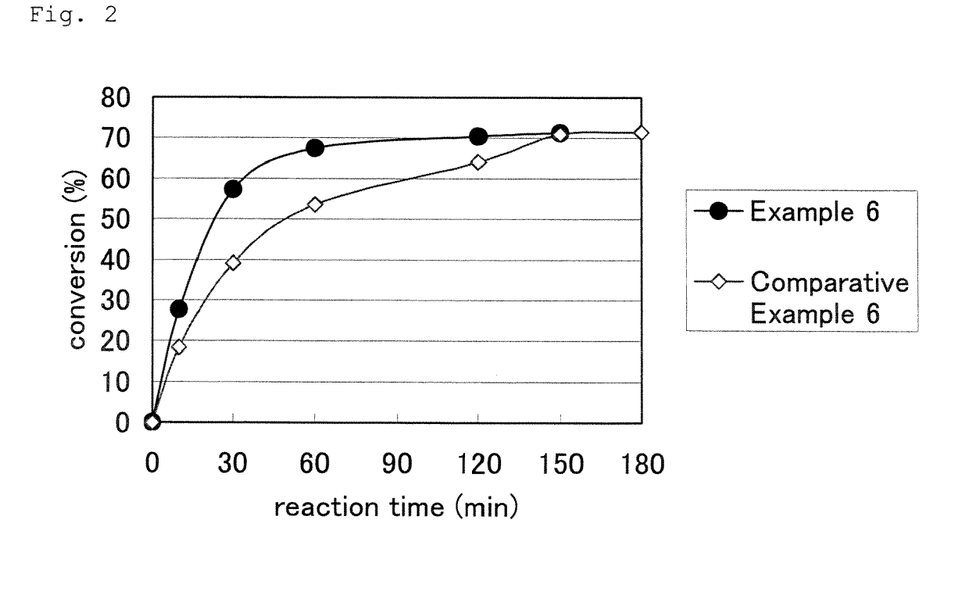
FIG. 2 shows results of Example 6 and Comparative Example 6.

The results of Example 6 and Comparative Example 6 shown in FIG. 2 indicate that the activity of the catalyst activity remains higher when the mixture of the present invention is used (Example 6) than when Material 2 is directly used (Comparative Example 6). To be more specific, it takes approximately a third part time to reach the 65% conversion in Example 6 than it takes in Comparative Example 6.

Example 7

The reaction and analysis were conducted in the same manner as in Example 6, except that the temperature was increased to 100° C., rather than 90° C., over the 50-minute period. The results are shown in FIG. 3.

Comparative Example 7

The reaction and analysis were conducted in the same manner as in Example 7, except that the mixture obtained in Example 2 (500 ml; 310 g) was replaced with Material 2 (500 ml; 310 g). The results are shown in FIG. 3.

Figure 3:
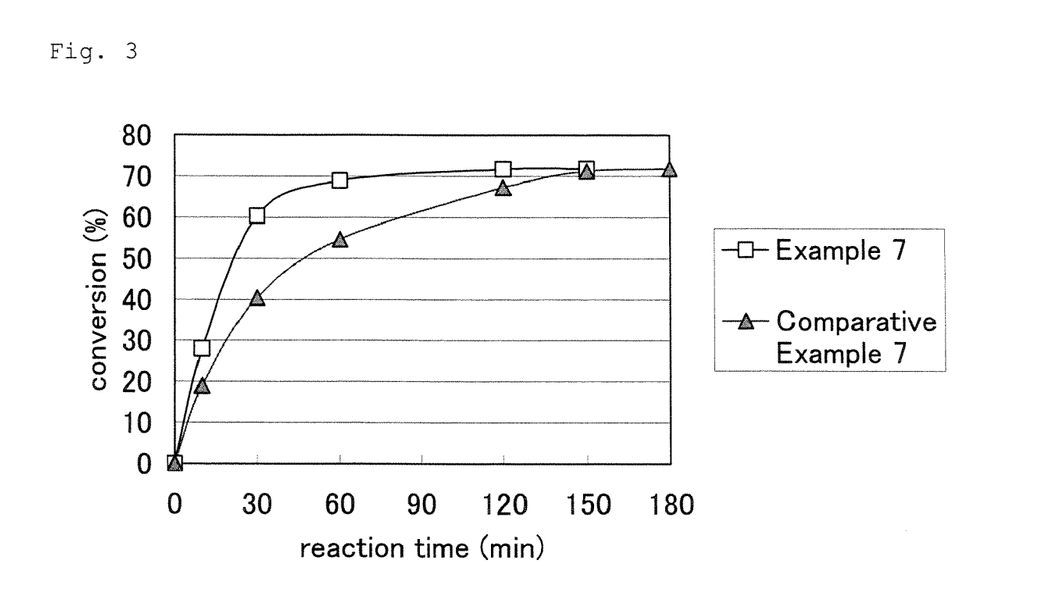
FIG. 3 shows results of Example 7 and Comparative Example 7.

The results of Example 7 and Comparative Example 7 shown in FIG. 3 indicate that the activity of the catalyst remains higher when the mixture of the present invention is used (Example 7) than when Material 2 is directly used (Comparative Example 7). To be more specific, it takes approximately a third part time to reach the 65% conversion in Example 7 than it takes in Comparative Example 7.

Example 8

The reaction and analysis were conducted in the same manner as in Example 5, except that the 3.84 g 28% methanol solution of sodium methoxide (equivalent to 1.07 g (19.9 mmol) sodium methoxide) and the 925 g (1.17 L, 28.9 mol) methanol were replaced with 4.84 g 28% ethanol solution of sodium ethoxide (equivalent to 1.35 g (19.9 mmol) sodium ethoxide) and 1377 g (29.9 mol) ethanol, respectively. The results are shown in FIG. 4.

Comparative Example 8

The reaction and analysis were conducted in the same manner as in Example 8, except that the mixture obtained in Example 2 (500 ml; 310 g) was replaced with Material 2 (500 ml; 310 g). The results are shown in FIG. 4.

Figure 4:
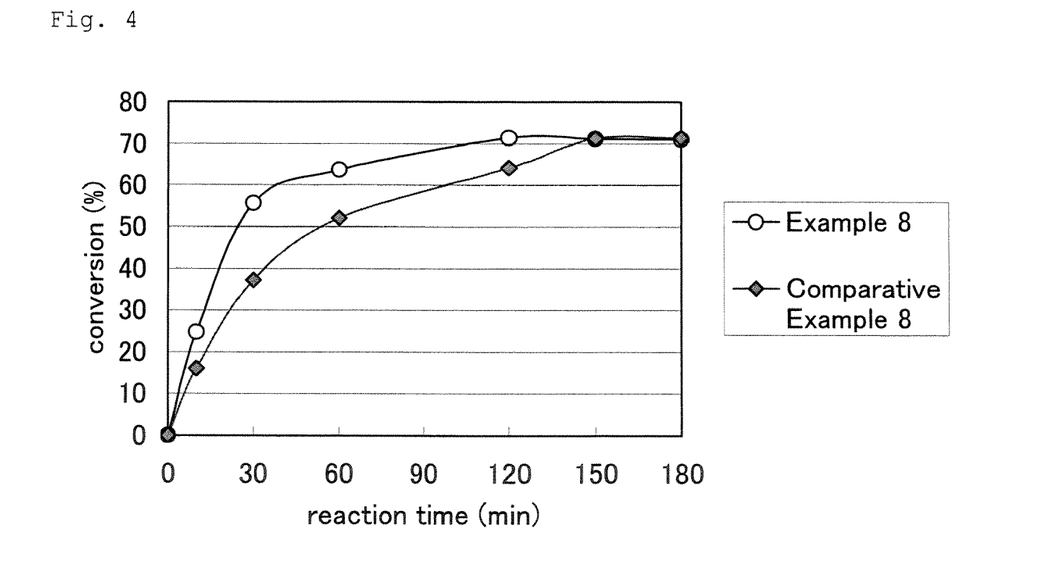
FIG. 4 shows results of Example 8 and Comparative Example 8.

The results of Example 8 and Comparative Example 8 shown in FIG. 4 indicate that the activity of the catalyst remains higher when the mixture of the present invention is used (Example 8) than when Material 2 is directly used (Comparative Example 8). To be more specific, it takes approximately half time as long to reach the 65% conversion in Example 8 as it takes in Comparative Example 8.

Example 9

The reaction and analysis were conducted in the same manner as in Example 5, except that the 3.84 g 33% methanol solution of potassium methoxide (equivalent to 1.07 g (19.9 mmol) sodium methoxide) was replaced with 4.22 g 28% ethanol solution of sodium ethoxide (equivalent to 1.40 g (19.9 mmol) potassium methoxide). The results are shown in FIG. 5.

Comparative Example 9

The reaction and analysis were conducted in the same manner as in Example 9, except that the mixture obtained in Example 2 (500 ml; 310 g) was replaced with Material 2 (500 ml; 310 g). The results are shown in FIG. 5.

Figure 5:
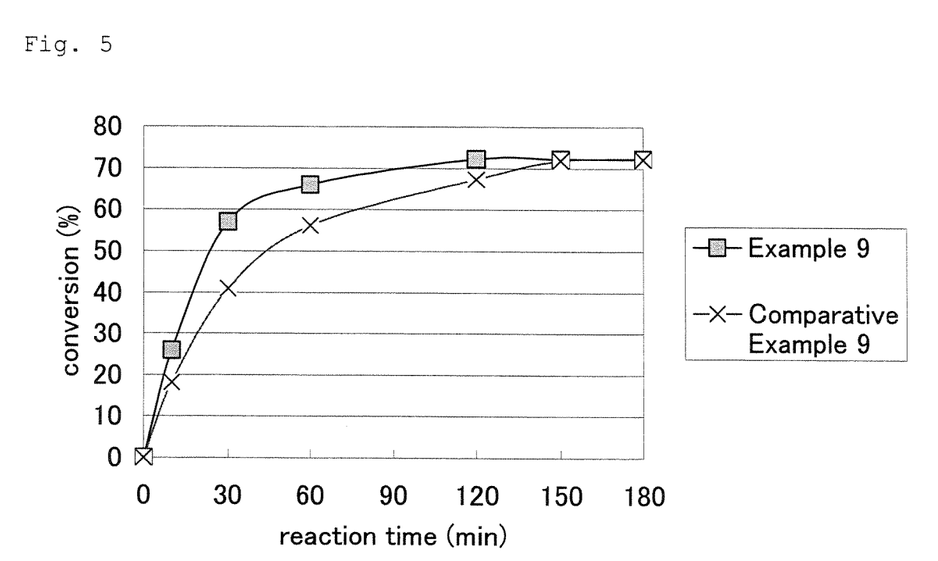
FIG. 5 shows results of Example 9 and Comparative Example 9.

The results of Example 9 and Comparative Example 9 shown in FIG. 5 indicate that the activity of the catalyst remains higher when the mixture of the present invention is used (Example 9) than when Material 2 is directly used (Comparative Example 9). To be more specific, it takes approximately half time as long to reach the 65% conversion in Example 9 as it takes in Comparative Example 9.

In summary, the use of the mixtures of the present invention in each case allows the activity of the catalyst to be maintained significantly higher as compared to the conventional C4 fraction. Thus, the mixtures of the present invention, which are prepared through a simple process, can be used as a starting material in the production of ether (II) to maintain the activity of relatively expensive palladium catalysts. As a result, significant cost reduction is achieved.

The invention claimed is:

1. A process for producing an ether represented by the following general formula (II):

(II)

wherein $R^a$ is a substituted or unsubstituted alkyl group or a substituted or unsubstituted aryl group, comprising:
providing a mixture comprising 25 to 80 mass % 1,3-butadiene, 13 to 68 mass % butenes, 2 to 15 mass % butanes, 10 ppm or less butynes and 5 to 100 ppm methylallene;
providing a catalyst solution comprising a hydroxyl compound represented by the following general formula (I):

wherein $R^a$ is a substituted or unsubstituted alkyl group or a substituted or unsubstituted aryl group, a palladium catalyst, a nitrogen-containing heterocyclic aromatic compound, an isocyanide compound, and a base; and
feeding to a reactor the mixture and the catalyst solution to carry out a telomerization process.

* * * * *